(12) United States Patent
Stauffer

(10) Patent No.: US 8,440,868 B2
(45) Date of Patent: May 14, 2013

(54) MANUFACTURE OF METHANOL

(76) Inventor: John E. Stauffer, Greenwich, CT (US)

( * ) Notice: Subject to any disclaimer, the term of this patent is extended or adjusted under 35 U.S.C. 154(b) by 0 days.

(21) Appl. No.: 13/412,685

(22) Filed: Mar. 6, 2012

(65) Prior Publication Data

US 2012/0259144 A1   Oct. 11, 2012

Related U.S. Application Data

(63) Continuation-in-part of application No. 13/080,857, filed on Apr. 6, 2011.

(51) Int. Cl.
*C07C 29/50* (2006.01)
*C07C 29/48* (2006.01)

(52) U.S. Cl.
USPC .......................... 568/910; 568/891; 568/893

(58) Field of Classification Search ................... 568/910, 568/891, 893
See application file for complete search history.

(56) References Cited

U.S. PATENT DOCUMENTS

| | | | |
|---|---|---|---|
| 6,452,058 B1 * | 9/2002 | Schweizer et al. | 570/223 |
| 6,486,368 B1 * | 11/2002 | Zhou et al. | 568/893 |
| 7,696,390 B2 * | 4/2010 | Stauffer | 568/893 |

* cited by examiner

*Primary Examiner* — Elvis O Price
(74) *Attorney, Agent, or Firm* — Young Basile Hanlon & MacFarlane PC

(57) ABSTRACT

An alcohol such as methanol is produced from an alkane such as methane and oxygen in a single step process using a heterogeneous catalyst. The catalyst comprises the chloride salts of copper, potassium, lead and zinc.

8 Claims, 1 Drawing Sheet

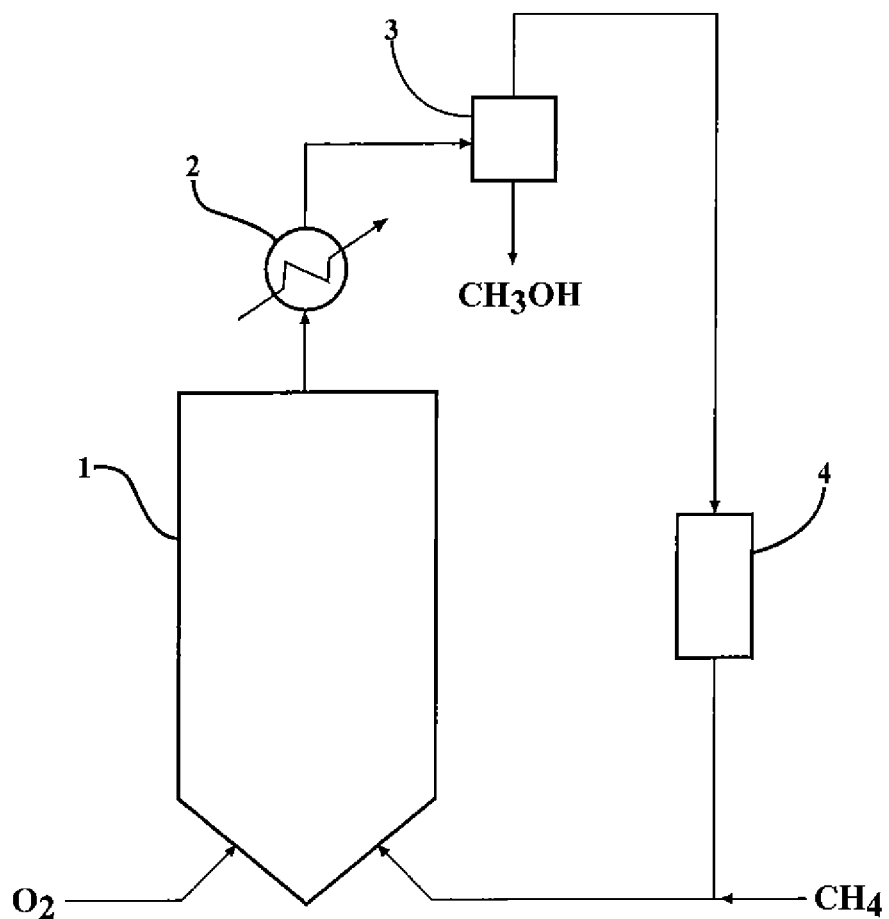

MANUFACTURE OF METHANOL

CROSS-REFERENCE TO RELATED APPLICATION

This application is a continuation-in-part of the co-pending U.S. patent application Ser. No. 13/080,857 filed Apr. 6, 2011. The content of U.S. patent application Ser. No. 13/080,857 is incorporated herein by reference.

FIELD OF THE INVENTION

The invention relates to a process for manufacturing methanol from methane. In a single step process, a stream of methane and oxygen is passed over a heterogeneous catalyst to convert these gases to methyl alcohol. The process is characterized by high conversions and yields.

BACKGROUND OF THE INVENTION

The only commercial process for the production of methanol starts with the generation of synthesis gas containing carbon monoxide and hydrogen. When natural gas is the raw material, synthesis gas can be formed by reacting the methane in the natural gas with carbon dioxide and water over a catalyst at elevated temperatures. The resulting synthesis gas is converted to methanol at high pressures using a suitable catalyst.

Numerous improvements have been made in the methanol process since it was introduced in the 1920's. Nevertheless, this process is handicapped by high capital investment to produce the synthesis gas and by the need to operate the conversion step at elevated pressure to overcome the unfavorable equilibrium conditions.

Certain inefficiencies are inherent in the present process for producing methanol. The process is wasteful of energy in the sense that it first transforms methane in an oxidative reaction to carbon monoxide, which in turn must be reduced to methanol. The direct selective transformation of methane to methanol is therefore a highly desirable goal and one that has been pursued by numerous researchers.

The main problem associated with the direct oxidation of methane to methanol is the unavoidable formation of byproducts including formaldehyde, formic acid, carbon monoxide, and the ultimate oxidation product, carbon dioxide. The challenge therefore has been to identify a catalyst that is highly selective for the formation of methanol. To date, such catalysts as molybdenum and vanadium oxides have been found to be the most effective but still fall short of industrial expectations.

Other applications of the present invention will become apparent to those skilled in the art when the following description of the best mode contemplated for practicing the invention is read in conjunction with the accompanying drawings.

SUMMARY OF THE INVENTION

It is an object of the present invention to provide an effective process for the direct; i.e., one-step, conversion of an alkane to an alcohol; e.g., the conversion of methane to methanol using a robust catalyst which offers high selectivity under operating conditions.

In accordance with an illustrative embodiment of the invention, a feed stream containing methane and oxygen is passed over a heterogeneous catalyst to convert the gases directly to the methanol product. The catalyst comprises the chlorides of copper, potassium, lead and zinc. These salts are components of a mix that is molten under operating temperatures. The salt melt can be employed alone of deposited on an inert carrier such as Kieselguhr, silica gel, or activated carbon.

The process contemplates the use of any reactor design including molten salt, fixed bed, or fluidized bed. The latter type, however, is preferred because of its simplicity and its ability to control the reaction temperature.

Operating conditions for the process are as follows: pressure between 1 and 20 atmospheres and temperatures in the range of 375° C. to 475° C. Either stoichiometric quantities of feed gases may be used or an excess of oxygen or methane may be employed. Air or various oxygen-to-air ratios may also be used.

The present invention is a special case of the general procedure for the manufacture of alcohol from an alkane in a one-step process. Besides methanol, other alcohols can be produced by this process including ethanol, propanol, and butanol. In each instance, the starting material is the corresponding alkane, namely ethane, propane, or butane.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawings wherein like reference numerals refer to like parts throughout the several views and wherein:

FIG. 1 is a drawing showing the principal features of the process. The reactor design that is chosen is a fluidized bed reactor.

DETAILED DESCRIPTION OF THE ILLUSTRATIVE EMBODIMENT

The advantages of the present invention are best understood through an appreciation of the chemistry involved. The following reactions are postulated as taking place in the presence of the molten salt catalyst.

$$CH_4 + Cl_2 \rightarrow CH_3Cl + HCl \tag{1}$$

$$CH_3Cl + H_2O \rightarrow CH_3OH + HCl \tag{2}$$

$$2HCl + 0.5 O_2 \rightarrow Cl_2 + H_2O \tag{3}$$

In the above equations, $CH_4$ represents the raw material methane, $Cl_2$ is chlorine, $CH_3Cl$ is methyl chloride, HCl is hydrogen chloride, $H_2O$ is water, $O_2$ is oxygen, and $CH_3OH$ is the product methanol.

When the above equations are combined, the following reaction is obtained.

$$CH_4 + 0.5 O_2 \rightarrow CH_3OH \tag{4}$$

From equation 4, it is observed that all the chlorine compounds are consumed within the process, Likewise, the formation of water is balanced by its consumption.

Initially, in order to get the reactions started, some chlorine must be present. This chlorine is supplied by the copper chloride, specifically cupric chloride of $CuCl_2$ in the catalyst. The resulting cuprous chloride of CuCl is converted back to cupric chloride by first reacting it with oxygen to form cupric oxychloride $Cu_2Cl_2O$. This intermediate is then reacted with hydrogen chloride to regenerate cupric chloride and water.

It is apparent that copper chloride is a necessary component of the catalyst. This is the well-known Deacon catalyst first used to produce chlorine from hydrogen chloride and air (equation 3). It is also the catalyst used in oxychlorination reactions where a hydrocarbon is introduced into the reaction. In the present invention, that hydrocarbon is methane (equation 1).

Another key component of the catalyst system is potassium chloride. Although this compound does not react with any of the compounds present, it lowers the melting point of the catalyst mix. Potassium chloride forms a eutectic mix with copper chloride and thus, when added in the proper proportion to the catalyst mix, will ensure its liquidity. This feature is important because it is believed to enhance the catalyst activity.

Lead chloride in the catalyst mix functions as a negative catalyst. As noted in the prior art, one of the chief hurdles to developing a viable process was the formation of byproducts. Lead compounds act by inhibiting the combustion of hydrocarbons. It therefore suppresses the formation of formaldehyde, carbon monoxide and carbon dioxide in the present invention.

Finally, zinc chloride is a required addition to the catalyst melt. In the manufacture of methyl chloride from methanol and hydrogen chloride, zinc chloride with or without cuprous chloride is used as the catalyst. Equation 2 is the reverse reaction, and thus, it is likewise promoted by zinc chloride.

One of the challenges of the present invention is controlling the reaction temperature within a narrow range. The overall reaction of equation 4 is highly exothermic, and therefore the heat of reaction must be removed. This objective may be achieved by using a fluidized bed reactor, which has proven to provide superior temperature stability. Further assistance comes from operating at elevated pressures. Heat transfer through the gases in the reactor can be improved by employing moderate pressure up to about 20 atmospheres.

The present invention is best illustrated by the drawing in FIG. 1. In this diagram, fluidized bed reactor 1 holds the catalyst, which is fluidized by the reactant gas streams oxygen and methane. Exit gases from the reactor are cooled by condenser 2 before passing to the phase separator 3 where the product methanol is recovered. Unreacted methane is recycled by blower/compressor 4 to the bottom of the reactor.

EXAMPLE

Methane, hydrogen chloride and oxygen were reacted together over a catalyst to produce chlorinated methane products. The catalyst comprised 40 mol percent copper, 30 mol percent potassium, 10 mol percent sodium and 20 mol percent lead. The catalyst was prepared from the corresponding nitrate salts by exposing the mix to hydrogen chloride for several hours at an elevated temperature.

During the experiment, the reactor temperature was maintained between 450° C. and 453° C. and the pressure was kept at 1 atmosphere. Under steady state conditions, 16.8 percent of the methane was converted by methyl chloride, 8.6 percent to methylene chloride, 3.3 percent to chloroform, 0.2 percent to carbon tetrachloride and 71.2 percent remained reacted. No carbon monoxide or carbon dioxide was detected in the effluent gases.

What is claimed is:

1. A process for the manufacture of methanol from methane and oxygen in a single step wherein methane and oxygen are reacted over a heterogeneous catalyst comprising the chlorides of copper, potassium, lead and zinc to produce methanol, the reaction being conducted at a temperature in the range of 375° C. to 475° C. and under a pressure from 1 atmosphere to 20 atmospheres.

2. The process according to claim 1 in which the reaction is carried out in a fluidized bed reactor.

3. The process according to claim 1 in which an excess of methane is used.

4. The process according to claim 1 in which oxygen is supplied by air.

5. A process for the manufacture of alcohol from an alkane and oxygen in a single step wherein the alkane and oxygen are reacted over a heterogeneous catalyst comprising the chlorides of copper, potassium, lead and zinc to produce alcohol, the reaction being conducted at a temperature in the range of 375° C. to 475° C. and under a pressure from 1 atmosphere to 20 atmosphere.

6. The process according to claim 5 in which the alcohol is ethanol and the alkane is ethane.

7. The process according to claim 5 in which the alcohol is propanol and the alkane is propane.

8. The process according to claim 5 in which the alcohol is butanol and the alkane is butane.

* * * * *